United States Patent [19]

Rudershausen

[11] Patent Number: 4,837,370
[45] Date of Patent: Jun. 6, 1989

[54] MANUFACTURE OF DIFLUOROCHLOROMETHANE

[75] Inventor: Charles G. Rudershausen, Kennett Square, Pa.

[73] Assignee: E. I. Du Pont De Nemours and Company, Wilmington, Del.

[21] Appl. No.: 211,104

[22] Filed: Jun. 17, 1988

Related U.S. Application Data

[63] Continuation of Ser. No. 85,304, Aug. 12, 1987, abandoned, which is a continuation of Ser. No. 889,467, Jul. 25, 1986, abandoned.

[51] Int. Cl.$^4$ .................. C07C 17/20; C07C 17/24; C07C 19/02; C07C 19/00
[52] U.S. Cl. ................................................ 570/163
[58] Field of Search ........................................ 570/163

[56] References Cited

U.S. PATENT DOCUMENTS

| 3,087,976 | 4/1986 | Hauptschein et al. | 260/653 |
| 3,651,156 | 3/1972 | Scherer et al. | 570/163 |
| 4,678,859 | 7/1987 | Rudershausen | 570/163 |

FOREIGN PATENT DOCUMENTS 1422476 11/1965 France .

OTHER PUBLICATIONS

Translation of French Pat. No. 1,422,476, granted 11-15-1965.

*Primary Examiner*—J. E. Evans

[57] ABSTRACT

A vapor phase process is disclosed for the selective disproportionation of fluorodichloromethane to difluorochloromethane and chloroform using a solid catalyst of an activated mixture of iron oxide and rare earth oxides.

6 Claims, No Drawings

MANUFACTURE OF DIFLUOROCHLOROMETHANE

This application is a continuation, of application Ser. No. 07/085,304 filed Aug. 12, 1987, now abandoned, which is a continuation of Ser. No. 889,467, filed July 25, 1986, now abandoned.

BACKGROUND OF THE INVENTION

This invention relates to a vapor phase process for the selective disproportionation of fluorodichloromethane ($CHCl_2F$) to difluorochloromethane ($CHClF_2$) and chloroform ($CHCl_3$) using a solid catalyst of an activated mixture of iron oxide and rare earth oxides.

Generally, fluorinated haloalkanes are produced commercially by liquid phase reaction of anhydrous hydrogen fluoride (HF) with chloroalkanes in the presence of a catalyst as disclosed in Daudt et al., U.S. Pat. Nos. 2,005,705 and 2,005,708. This reaction usually occurs at superatmospheric pressure and is illustrated by the following equation using chloroform as the representative haloalkane:

$$XHF + CHCl_3 \rightarrow CHCl_{3-X}F_X + XHCl$$

antimony
chloride wherein $X = 1$ to 3. A mixture of products is obtained, the amount of each product produced depends on process conditions and feed ratios. It is not possible, however, to completely avoid the production of undesirable products through control of process parameters. In the above illustration trifluoromethane ($CHF_3$) is an undesired by-product with a vapor pressure which is too high for significant commercial use; its fluorine values are normally wasted.

The conventional process used to produce fluorinated haloalkanes employs anhydrous HF, a particularly corrosive chemical which is very hazardous to handle. Also, hydrochloric acid (HCl) is a by-product and must be disposed of, either by considerable purification to eliminate residual halocarbons prior to sale, or by neutralization and disposal at significant expense and environmental risk. Finally, the antimony-based catalyst eventually loses both activity and selectivity and must be disposed of with extreme caution because of environmental concerns related particularly to possible contamination of surface and subsurface waters.

French Patent No. 1,422,476 describes a catalyst for hydrofluorination of chlorocarbons to a range of fluorinated products. For example, anhydrous HF is reacted with chloroform in the vapor phase over a catalyst of iron and rare earth oxides to produce $CHCl_2F$, $CHClF_2$, $CHF_3$ and hydrochloric acid.

U.S. Pat. No. 3,087,967 discloses the conversion of monohydrofluorochloromethanes with one or two fluorine atoms using an activated alumina catalyst. The process proceeds to high conversions of $CHF_3$ with little conversion of $CHCl_2F$ and $CHClF_2$.

The present invention provides a process whereby the product $CHClF_2$, widely used as a commercial refrigerant and for other commercial purposes, can be manufactured efficiently and selectively under mild conditions. In addition, hazards in handling and the need for strict environmental controls imposed by the use of HF and the recovery and disposal of HCl and the antimony catalyst are avoided.

More specifically, the object of the present invention is to produce $CHClF_2$ selectively and efficiently by an acid-free process, while using a catalyst whose eventual disposal poses little or no difficulty or environmental problems.

SUMMARY OF THE INVENTION

In accordance with the present invention, an efficient process has been discovered by which difluorochloromethane is selectively and efficiently manufactured without HF feed or HCl byproduct formation and at modest reaction conditions comprising contacting fluorodichloromethane with an effective amount of a catalyst comprising an activated mixture of iron oxide and rare earth oxides at effective process conditions to produce a reaction product containing difluorodichloromethane and chloroform. This selective reaction may be summarized as follows:

$$2CHCl_2F \rightarrow CHClF_2 + CHCl_3$$

Thereafter, difluorodichloromethane and chloroform can be separated from the reaction product and the difluorodichloromethane can be isolated.

DETAILED DESCRIPTION OF THE INVENTION

The catalyst of this invention can contain different amounts of iron oxide and the oxides of various rare earth (RE) metals, such as scandium, yttrium, lanthanum, cerium, praseodymium, neodymium, illinium, samarium, europium, gadolinium, terbium, dysoprosium, holmium, erbium, thulium, ytterbium and lutecium. The catalyst can also contain one or more oxides of various other metals, including metals such as cobalt, zirconium, manganese, thorium, and aluminum. However, the catalyst must contain some iron oxide and one or more oxides of various rare earths. Naturally occurring mixtures of rare earth oxides can be used as well as commercial preparations of these rare earth oxides.

One particularly preferred embodiment of the invention involves preparation of a coprecipitated catalyst by simultaneously combining aqueous solutions of iron nitrate ($Fe(NO_3)_3 \cdot 9H_2O$), a mixture of lanthanum-RE nitrates ($La-RE(NO_3)_3 \cdot 6H_2O$) and ammonium hydroxide ($NH_4OH$). The mixture of lanthanum-RE nitrates can be a mixture which is sold by Molycorp (subsidiary of Union Oil Co.) and designated in Molycorp's catalog of lanthanum-RE nitrate solutions as No. 5247. The specification and typical composition of No. 5247 is listed by Molycorp as follows:

| No. 5247* | |
|---|---|
| | Specification (wt.) |
| Total Rare Earth Oxides (REO's)** | 39.0% min. |
| $CeO_2$/REO | 1.0% max. |
| $Na_2O$ | 0.2% max. |
| CaO + SrO | — |
| Cl | 0.1% max. |
| Water Insolubles | 0.1% max. |
| pH of Solution | 1.5 max. |
| | Typical (wt.) |
| $Fe_2O_3$ | 0.02% |
| Heavy Metals (Pb + V + Ni + Cu) | 0.01% |
| MgO | 0.05% |

*As Solution: Concentration of $La-RE(NO_3)_3 \cdot 6H_2O$ solids in solution 55–65%.
**Typical Composition of the contained Rare Earth Oxides:

-continued

| No. 5247* | |
|---|---|
| Oxide | wt. |
| Lanthanum ($La_2O_3$) | 0.66% |
| Neodymium ($Nd_2O_3$) | 24.0% |
| Cerium ($CeO_2$) | 0.7% (1% max.) |
| Praseodymium ($Pr_6O_{11}$) | 8.2% |
| Other REO | 1.1% |
| Total | 100.0% |

The precipitate which is formed is water washed, dried and calcined to yield a catalyst containing iron oxide and rare earth oxides (REO's). After calcination, the catalyst can be crushed and screened to obtain a preferred particle size, such as 10 to 20 mesh.

Other methods can be used to prepare the catalyst of this invention and are well known to those skilled in the art of catalyst manufacture and include but are not limited to techniques such as physically mixing iron oxide and rear earth oxides together and thereafter pelletizing this mixture and using the pellets as formed or crushed to a desired particle size. Another method of preparationis to extrude a suitable slurry containing the desired iron nitrates and rare earth nitrates and, thereafter, to calcine this mixture and, if desired, crush to reduce particle size. Also, an inert surface or support could be impregnated with an aqueous solution of iron nitrate and rare earth nitrates and thereafter the surface could be dried and calcined to remove the nitrates so as to leave iron oxide and rare earth oxides on the surface.

After preparation, the catalyst must be activated before use. This activation can be accomplished by any technique which contacts the catalyst with a vaporized fluorine-containing compound. One preferred method of activating the catalyst involves treating it in a reactor to be used for the disproportionation of this invention with a vapor stream of either a fluorine-containing halocarbon or a mixture of HF and nitrogen, while gradually increasing the temperature to at least about 300 degrees Celsius and maintaining this temperature for at least one hour. Preferably, the temperature during this activation should be increased to about 450 degrees Celsius for a period of at least about one hour. After this activation, the catalyst is cooled and can be left in the reactor equipped with feed parts by which $CHCl_2F$ can be introduced.

$CHCl_2F$ can then be fed to the reactor to contact an effective amount of activated catalyst at effective process conditions to convert the $CHCl_2F$ to difluorochloromethane and chloroform. By effective amount of activated catalyst and effective process conditions is meant an amount of activated catalyst and process conditions which cause difluorochloromethane and chloroform to be formed as the primary products of the reaction.

The operable ranges of process conditions include temperatures of 50 to 300 degrees Celsius and contact times of 0.1 to 10 seconds based on the volume of feed and the catalyst bed. The process is operable using subatmospheric, atmospheric or superatmospheric pressure. The particular pressure used may be selected giving due consideration to the technique to be used for separating and isolating the $CHClF_2$ to be formed. The reaction is preferably operated at about 0.1 to 10 atmospheres pressure. The preferred temperature range is about 75 to 200 degrees Celsius, and preferred catalyst contact times are between about 0.1 to 5 seconds. The particularly preferred conditions are a temperature of 200 degrees Celsius, a catalyst contact time of 0.4 second and atmospheric pressure.

The process of this invention may use any appropriate reactor. A shell and tube reactor is particularly desirable in which the catalyst is contained in the tubes from which the heat of reaction is transferred to water on the shell side. If the reaction temperature is over 100 degrees Celsius, steam can be produced and the pressure selected to correspond to the reaction temperature desired in the catalyst bed.

Continuous or batch distillation can be used to separate the products and unreacted $CHCl_2F$, which can be recycled, if desired. Byproduct chloroform can be recovered and utilized in a separate process to produce further $CHCl_2F$, if desired.

The following examples illustrate particular aspects of the present invention:

| No. 5247* | |
|---|---|
| | Specification (wt.) |
| Total Rare Earth Oxides (REO's)** | 39.0% min. |
| $CeO_2$/REO | 1.0% max. |
| $Na_2O$ | 0.2% max. |
| CaO + SrO | — |
| Cl | 0.1% max. |
| Water Insolubles | 0.1% max. |
| pH of Solution | 1.5% max. |
| | Typical (wt.) |
| $Fe_2O_3$ | 0.02% |
| Heavy Metals (Pb + V + Ni + Cu) | 0.01% |
| MgO | 0.05% |

*As Solution: Concentration of La—RE$(NO_3)_3$.$6H_2O$ solids in solution 55–65%.
**Typical Composition of the contained Rare Earth Oxides:

| Oxide | wt. |
|---|---|
| Lanthanum ($La_2O_3$) | 66.0% |
| Neodymium ($Nd_2O_3$) | 4.0% |
| Cerium ($CeO_2$) | 0.7% (1% max.) |
| Praseodymium ($Pr_6O_{11}$) | 8.2% |
| Other REO | 1.1% |
| Total | 100.0% |

(c) 160 ml of 28% aqueous $NH_4OH$ in 800 ml of distilled water

The nitrate solutions were combined in a single separatory funnel; the ammonium hydroxide solution was charged to another separatory funnel. Each of these two funnels was equipped with rubber tubing extensions to the bottom of a 2-liter beaker outfitted with a magnetic stirring bar and a pH meter probe just over the stirring bar. Both the nitrate and the ammonium hydroxide solutions were separately preheated to 80 degrees Celsius and then discharged simultaneously over a period of about fifteen minutes at rates adjusted to keep the pH in the mixing zone between 8.5 and 9.5. After addition of the solutions was completed, stirring was continued for 1 hour while cooling to 65 degrees Celsius, after which the pH was adjusted back to 8.5 with incremental addition of ammonium hydroxide solution. The precipitate was vacuum-filtered, displacement-washed with 2 liters of distilled water heated to 65 degrees Celsius, vacuum-dried at 170 degrees Celsius and finally calcined for 6 hours at 500 degrees Celsius for a yield of 70 g of hard particles which were crushed and screened to a 10 to 20 mesh particle size range and used as described further herein. The catalyst contained oxides with approximately a 63:37 weight ratio of iron:rare earth metals.

Two cc of the catalyst were charged to a 7 cc Inconel reactor tube placed in a sand bath with temperature controlled electric heaters. The catalyst was heated to 150 degrees Celsius by passing heated nitrogen over the catalyst for a two hour period (100 std. cu. cm. per min.). Thereafter, the catalyst was activated with vaporized anhydrous HF which was added at 30 std. cu. cm. per min. (sccm) while continuing the nitrogen addition at the original rate during further heating to 300 degrees Celsius over a 1 hour period. The ntirogen and HF flows were then reduced to 25 sccm each while slowly cooling to 100 degrees Celsius.

EXAMPLE 2

The activated catalyst (2 cc) as prepared in Example 1 was left in the 7 cc Inconel reactor already equipped with feed parts. $CHCl_2F$ was fed to the reactor as a vapor from a cylinder through a mass flow meter at 168 cc/min (1 atm, 20 degrees Celsius). The reactor was maintained at essentially 1 atmosphere pressure and 100 degrees Celsius in a thermally controlled fluidized sand bath. Contact time in the 2 cc catalyst bed was a nominal 0.4 seconds based on 250 degrees Celsius in the catalyst bed and 1 atmosphere pressure. Product effluent was measured with a flame ionization gas chromatograph. As shown in the Table for this example, selectivity was excellent (98% yield), with only 0.9% conversion lost to $CHF_3$. Conversion was 50%, showing high catalyst activity in addition to excellent selectivity.

EXAMPLES 3-5

Using the catalyst of Example 1 and the procedures of Example 2 modified to illustrate amenability to various temperatures (75 to 200 degrees Celsius) and retention times (0.4 to 3 seconds, as defined in Example 2), good activity and selectivity are shown in the Table.

The description and examples are not intended to limit the scope of the invention, especially with respect to specific composition and proportions of the iron oxide and rare earth oxides used or the mode of catalyst preparation.

TABLE

| Example | T* | CT** | Percent Molar Effluent Composition | | | |
|---|---|---|---|---|---|---|
| | | | $CHCl_3$ | $CHCl_2F$ | $CHClF_2$ | $CHF_3$ |
| 2 | 100 | 0.4 | 27 | 50 | 22 | 0.9 |
| 3 | 75 | 0.4 | 25 | 55 | 20 | 0.5 |
| 4 | 200 | 0.4 | 30 | 45 | 25 | 0.7 |
| 5 | 75 | 3 | 35 | 36 | 28 | 0.8 |

*Degrees Celsius
**Catalyst contact time at 250° Celsius and 1 atm., sec.

I claim:

1. A process comprising contacting, in the vapor phase, fluorodichloromethane with an effective amount of a catalyst comprising an activated mixture of iron oxide and rare earth metal oxides, said rare earth metal selected from the group consisting of scandium, yttrium, lanthanum, cerium, praseodymium, neodymium, illinium, samarium, europium, gadolinium, terbium, dysprosium, holmium, erbium, thulium, ytterbium and lutecium, at a temperature of 50 to 300 degrees Celsius and a contact time of 0.1 to 10 seconds based on the volume of feed and the catalyst bed to produce a reaction product containing primarily difluorochloromethane and chloroform, said contacting step conducted without HF feed.

2. The process of claim 1 wherein the temperature is about 75 to 200 degrees Celsius, the pressure is about 0.5 to 10 atmospheres, and the period of time the fluorodichloromethane is in contact with the activated catalyst is about 0.1 to 10 seconds.

3. The process of claim 1 wherein the temperature is about 200 degrees Celsius, the pressure is about 1 atmosphere, and the period of time the fluorodichloromethane is in contact with the activated catalyst is about 0.4 second.

4. The process of claim 1 wherein the catalyst consists essentially of an activated mixture of iron oxide and rare earth oxides.

5. The process of claim 1 wherein the activated catalyst includes at least one member selected from the group consisting of oxides of cobalt, zirconium, manganese, thorium, and aluminum.

6. The process of claim 1 wherein the catalyst is used on a support.

* * * * *